United States Patent
Badylak

(10) Patent No.: US 7,815,686 B2
(45) Date of Patent: Oct. 19, 2010

(54) VASCULARIZATION ENHANCED GRAFT CONSTRUCTS

(75) Inventor: Stephen F. Badylak, West Lafayette, IN (US)

(73) Assignees: Purdue Research Foundation, West Lafayette, IN (US); Clarian Health Partners, Inc., Indianapolis, IN (US)

( * ) Notice: Subject to any disclaimer, the term of this patent is extended or adjusted under 35 U.S.C. 154(b) by 0 days.

(21) Appl. No.: 10/428,350

(22) Filed: May 2, 2003

(65) Prior Publication Data

US 2003/0216811 A1 Nov. 20, 2003

Related U.S. Application Data

(60) Provisional application No. 60/377,566, filed on May 2, 2002.

(51) Int. Cl.
*A61F 2/02* (2006.01)
*A01N 65/00* (2006.01)

(52) U.S. Cl. .................... 623/23.72; 424/93.7

(58) Field of Classification Search .............. 424/93.1, 424/520, 550, 551; 623/23.72, 23.76
See application file for complete search history.

(56) References Cited

U.S. PATENT DOCUMENTS

| | | | |
|---|---|---|---|
| 4,829,000 A | 5/1989 | Kleinman et al. | |
| 4,902,508 A | 2/1990 | Badylak et al. | |
| 4,956,178 A | 9/1990 | Badylak et al. | |
| 5,281,422 A | 1/1994 | Badylak et al. | |
| 5,352,463 A | 10/1994 | Badylak et al. | |
| 5,554,389 A | 9/1996 | Badylak et al. | |
| 5,641,518 A | 6/1997 | Badylak et al. | |
| 5,863,531 A | 1/1999 | Naughton et al. | |
| 5,885,619 A | 3/1999 | Patel et al. | |
| 5,945,101 A | 8/1999 | Berg et al. | |
| 5,955,110 A | 9/1999 | Patel et al. | |
| 6,022,743 A * | 2/2000 | Naughton et al. | 435/395 |

(Continued)

FOREIGN PATENT DOCUMENTS

WO 98/06445 2/1998

(Continued)

OTHER PUBLICATIONS

"Endothelial Implants Inhibit Intimal Hyperplasia After Porcine Angioplasty," Helen M. Nugent et al., *Circulation Research*, Mar. 5, 1999, vol. 84, No. 4, p. 384-391.

(Continued)

*Primary Examiner*—Thomas J Sweet
(74) *Attorney, Agent, or Firm*—Barnes & Thornburg LLP

(57) ABSTRACT

An intestinal submucosa tissue graft construct for use in repairing diseased or damaged tissues is provided. The graft construct comprises vertebrate intestinal submucosa tissue, added endothelial cells, and at least one additional preselected, exogenous population of cells which enhances initiation of the formation of vessel-like structures in the graft. The preselected population of cells can be a population of non-keratinized or keratinized epithelial cells or a population of mesodermally derived cells selected from the group consisting of fibroblasts, smooth muscle cells, skeletal muscle cells, cardiac muscle cells, multi-potential progenitor cells, pericytes, osteogenic cells, and any other suitable cell type, preferably selected based on the tissue to be repaired. Methods for enhancing the vascularization in vivo of these intestinal submucosa tissue graft constructs and for preparing these graft constructs are also provided.

33 Claims, 1 Drawing Sheet

U.S. PATENT DOCUMENTS

| | | | |
|---|---|---|---|
| 6,099,567 A * | 8/2000 | Badylak et al. | 623/11.11 |
| 6,171,344 B1 | 1/2001 | Atala | |
| 6,187,039 B1 | 2/2001 | Hiles et al. | |
| 6,206,931 B1 | 3/2001 | Cook et al. | |
| 6,241,981 B1 | 6/2001 | Cobb et al. | |
| 6,264,992 B1 * | 7/2001 | Voytik-Harbin et al. | 424/551 |
| 6,358,284 B1 | 3/2002 | Fearnot et al. | |
| 6,375,989 B1 | 4/2002 | Badylak et al. | |
| 6,379,710 B1 | 4/2002 | Badylak | |
| 6,419,920 B1 | 7/2002 | Mineau-Hanschke | |
| 6,475,232 B1 | 11/2002 | Babbs et al. | |
| 6,485,723 B1 * | 11/2002 | Badylak et al. | 424/93.7 |
| 6,918,396 B1 | 7/2005 | Badylak et al. | |
| 6,962,814 B2 * | 11/2005 | Mitchell et al. | 435/402 |
| 7,087,089 B2 * | 8/2006 | Patel et al. | 623/23.72 |
| 7,175,841 B2 | 2/2007 | Badylak et al. | |
| 2003/0113302 A1 | 6/2003 | Revazova et al. | |
| 2003/0216811 A1 | 11/2003 | Badylak | |
| 2003/0216812 A1 | 11/2003 | Badylak | |
| 2004/0006395 A1 | 1/2004 | Badylak | |
| 2005/0202058 A1 | 9/2005 | Hiles | |
| 2006/0257377 A1 * | 11/2006 | Atala et al. | 424/93.7 |
| 2007/0141037 A1 | 6/2007 | Badylak et al. | |
| 2009/0324681 A1 | 12/2009 | Badylak | |

FOREIGN PATENT DOCUMENTS

| | | |
|---|---|---|
| WO | WO 98/25637 | 6/1998 |
| WO | WO 98/52637 | 11/1998 |
| WO | WO 00/15765 A1 | 3/2000 |
| WO | WO 00/62833 | 10/2000 |
| WO | WO 01/10355 | 2/2001 |
| WO | WO 01/45765 | 6/2001 |
| WO | WO 01/48153 A1 | 7/2001 |
| WO | WO 01/78754 | 12/2001 |
| WO | WO 02/07646 | 1/2002 |
| WO | WO 02/14480 | 2/2002 |
| WO | WO 02/20729 | 3/2002 |

OTHER PUBLICATIONS

"Three-Dimensional Imaging of Extracellular Matrix and Extracellular Matrix-Cell Interactions," Voytik-Harbin et al., Methods in Cell Biology, Ch. 27, vol. 43, pp. 583-597.

"Time-Lapse Confocal Reflection Microscopy of Collagen Fibrillogenesis and Extracellular Matrix Assembly In Vitro," A.O. Brightman et al., *Biopolymers*, vol. 54, 2000, pp. 222-234.

"Basal Lamina of Avian Ovarian Follicle: Influence On Morphology of Granulosa Cells In-Vitro," E.K. Asem et al., *Comparative Biochemistry and Physiology, Part C*, 125 (2000), pp. 189-201.

"Effect of Basal Lamina on Progesterone Production by Chicken Granulosa Cells In Vitro—Influence of Follicular Development," E.K. Asem et al., *Comparative Biochemistry and Physiology, Part C*, 125 (2000), pp. 233-244.

"PDGF, TGF-62, and Heterotypic Cell-Cell Interactions Mediate Endothelial Cell-Induced Recruitment of 10T1/2 Cells and Their Differentiation To A Smooth Muscle Fate," K.K. Hirschi et al., *The Journal of Cell Biology*, vol. 141, No. 3, May 4, 1998, pp. 805-814.

"Endothelial Cell Influences on Vascular Smooth Muscle Phenotype," J.H. Campbell et al., *Ann. Rev. Physiol.*, 1986, vol. 48, pp. 295-306.

Castano, E., et al., "Inhibition of DNA Synthesis by Aspirin in Swiss 3T3 Fibroblasts," Journal of Pharmacology and Experimental Therapeutics, vol. 280, No. 1, 1997, pp. 366-372.

Bhatia, S. N., et al., "Controlling Cell Interactions by Micropatterning in Co-Cultures: Hepatocytes and 3T3 Fibroblasts," Journal of Biomedical Materials Research, vol. 34, 1997, pp. 189-199.

Liu, C. H., et al., "Effects of Salvianolic Acid-A on NIH/3T3 Fibroblast Proliferation, Collagen Synthesis and Gene Expression," World J. Gastroentero, vol. 6, No. 3, 2000, pp. 361-364.

Keyes, K,. et al., "An In Vitro Tumor Model: Analysis of Angiogenic Factor Expression after Chemotherapy," Cancer Research, vol. 62, 2002, pp. 5597-5602.

Montesano, R., "Paracrine Induction of Angiogenesis in Vitro by Swiss 3T3 Fibroblasts", Journal of Cell Science, vol. 105, 1993, pp. 1013-1024.

Nerem, R., "Tissue Engineering: The Hope, The Hype and The Future" Tissue Engineering, vol. 12, No. 5, 2006, p. 1143-1150.

"Artificial Blood Vessel", English translation of Japanese Patent Application Publication No. 3-12169, 1991, 16 pages.

"In Vivo Plant Material", English translation of Japanese Patent Application Publication No. 1-170466, 1989, 13 pages.

Ho, M., et al., "Identification of Engothelial Cell Genes by Combined Database Mining and Microarray Analysis", Physiol Genomics, vol. 13, 2003, pp. 249-262.

Kubota Y. et al., "Role of Laminin and Basement Membrane in the Morphological Differentiation of Human Endothelial Cells into Capillary-like Structures," Journal of Cell Biology, 1988, vol. 107, pp. 1589-1598.

Maru et al., "An Oncogenic Form of the Flt-1 Kinase has a Tubulogenic Potential in a Sinusoidal Endothelial Cell Line," European Journal of Cell Biology, 2000, vol. 79, pp. 130-143.

Russmann H. et al., "Translocation of *Yersinia enterocolitica* through an Endothelial Monolayer by Polymorphonuclear Leukocytes," Infection and Immunity, vol. 64, No. 3, 1996, pp. 1016-1019.

Block, S., "Peroxygen Compounds," Sterilants, Disinfectants, and Antiseptics. A. By Chemical Type, S. Block, editor, 5th Edition 2001, pp. 185-204.

Denton, G.W., "Chlorhexidine," Sterilants, Disinfectants, and Antiseptics. A. By Chemical Type, S. Block, editor, 5th Edition 2001, pp. 321-336.

Yang, Eun Kyung, et al., "Tissue Engineered Artificial Skin Composed of Dermis and Epidermis", International Society for Artificial Organs, vol. 24, No. 1, Jan. 2000, pp. 7-17.

Badylak et al., "Endothelial cell adherence to small intestinal submucosa: an acellular bioscaffold" *Biomaterials*, vol. 20, 1999, pp. 2257-2263.

Office Action regarding Japanese Application Serial No. 2004-500666, Mailed from the Japanese Patent Office Aug. 25, 2009, pp. 1-3, English translation.

* cited by examiner

VASCULARIZATION ENHANCED GRAFT CONSTRUCTS

CROSS-REFERENCE TO RELATED APPLICATION

This application claims priority under 35 U.S.C. §119(e) to U.S. Provisional Application No. 60/377,566, filed May 2, 2002.

GOVERNMENT RIGHTS

Research relating to this invention was supported in part by the U.S. Government under Grant No. GM60691 awarded from the National Institutes of Health. The U.S. Government may have certain rights in this invention.

FIELD OF THE INVENTION

The present invention relates to vascularization enhanced submucosa tissue derived grafts and their use in repairing diseased or damaged tissues. More particularly, this invention is directed to vascularization enhanced intestinal submucosa tissue grafts that have been seeded with endothelial cells and at least one additional preselected, exogenous population of cells to enhance the repair capabilities of the intestinal submucosa tissue graft construct.

BACKGROUND AND SUMMARY OF THE INVENTION

The present invention is directed to a tissue graft construct comprising a vertebrate submucosa-derived matrix seeded with endothelial cells and at least one additional preselected, exogenous cell population for use in the repair of damaged or diseased tissues. The intestinal submucosa-derived matrices for use in accordance with the present invention preferably comprise highly conserved collagens, glycoproteins, proteoglycans, and glycosaminoglycans. The intestinal submucosa matrix for use in this invention is derived from intestinal submucosa tissue of a warm-blooded vertebrate.

The intestinal submucosa tissue graft constructs prepared in accordance with the present invention are substantially acellular matrices that provide a superior cell growth substrate resembling the matrix environment found in vivo. The natural composition and configuration of intestinal submucosa tissue provides a unique cell growth substrate that promotes the attachment and proliferation of cells in vitro and induces tissue remodeling when the graft constructs are implanted in vivo.

As a tissue graft material, intestinal submucosal tissue induces the growth of endogenous tissues upon implantation into a host (i.e., intestinal submucosa tissue induces remodeling). Intestinal submucosa tissue has been used successfully in vascular grafts, urinary bladder and hernia repair, replacement and repair of tendons and ligaments, and dermal grafts. The preparation and use of intestinal submucosa as a tissue graft composition is described in U.S. Pat. No. 4,902,508. When used in such an application the intestinal submucosa tissue graft constructs appear not only to serve as a matrix for the growth or regrowth of the tissues replaced by the graft constructs, but also to promote or to induce such growth or regrowth of endogenous tissue. Intestinal submucosa tissue can be used in an implantable sheet form or in injectable fluidized or gel forms for inducing the regrowth of endogenous tissues.

The present invention is directed to intestinal submucosa tissue graft constructs including added endothelial cells and at least one additional preselected, exogenous population of cells, and to methods of enhancing the vascularization of an intestinal submucosa tissue graft construct in vivo using these graft constructs. The vascularization enhanced intestinal submucosa tissue graft constructs are prepared by seeding the intestinal submucosa tissue in vitro with endothelial cells or endothelial cell precursors (e.g., progenitor cells or stem cells) and at least one additional preselected or predetermined cell type prior to implanting or injecting the intestinal submucosa tissue graft construct into the host.

In one embodiment is provided an intestinal submucosa tissue graft construct for use in repairing diseased or damaged tissues. The tissue graft construct comprises vertebrate intestinal submucosa tissue, added endothelial cells, and at least one additional preselected, exogenous population of cells.

In another embodiment a vascularized intestinal submucosa tissue graft construct is provided for use in repairing diseased or damaged tissues. The tissue graft construct comprises vertebrate intestinal submucosa tissue, added endothelial cells, and at least one additional preselected, exogenous population of cells wherein the endothelial cells have been cultured on the intestinal submucosa tissue for a time sufficient to form vessels or vessel-like structures in vitro.

In another embodiment a method is provided for enhancing the vascularization in vivo of an intestinal submucosa tissue graft construct. The method comprises the steps of seeding the intestinal submucosa tissue in vitro with a population of endothelial cells and at least one additional preselected, exogenous population of cells to form the graft construct, and implanting the graft construct into a vertebrate at a site in need of repair.

In yet another embodiment a method is provided for enhancing the vascularization in vivo of an intestinal submucosa tissue graft construct. The method comprises the steps of seeding the intestinal submucosa tissue in vitro with a population of endothelial cells and at least one additional preselected, exogenous population of cells, culturing in vitro the endothelial cells for a time sufficient to induce the formation of vessels or vessel-like structures or components, and implanting the graft construct into a vertebrate in a site in need of repair.

In either of these method embodiments the intestinal submucosa tissue can be seeded with the additional preselected population of cells after the intestinal submucosa tissue is seeded with the endothelial cells, the intestinal submucosa tissue can be seeded with the additional preselected population of cells before the intestinal submucosa tissue is seeded with the endothelial cells, or the intestinal submucosa tissue can be seeded with the endothelial cells and the additional preselected population of cells simultaneously or nearly simultaneously.

The endothelial cells can be cultured in vitro on the intestinal submucosa tissue for a time sufficient to induce the formation of vessels or vessel-like structures, or the endothelial cells can be cultured on the intestinal submucosa tissue for a time sufficient to expand the endothelial cells (i.e., allow the endothelial cells to divide at least one time) without forming vessels or vessel-like structures in vitro. Alternatively, the graft construct can be implanted without expanding the endothelial cells. In any of these embodiments the additional preselected population of cells may or may not be expanded (i.e., allowed to progress through at least one cell division cycle) prior to implanting the graft construct.

In still another embodiment a method is provided of preparing an intestinal submucosa tissue graft construct for use in repairing diseased or damaged tissues. The method comprises the step of seeding the intestinal submucosa tissue in vitro with a population of endothelial cells, and at least one additional preselected, exogenous population of cells to form the graft construct. The method can further comprise the step of culturing the endothelial cells in vitro on the intestinal submucosa tissue for a time sufficient to induce the formation of vessels or vessel-like structures.

In any of these embodiments the at least one additional cell population can comprise a population of non-keratinized or keratinized epithelial cells or a population of mesodermally derived cells selected from the group consisting of fibroblasts, smooth muscle cells, skeletal muscle cells, cardiac muscle cells, multi-potential progenitor cells (e.g., stem cells), pericytes, and osteogenic cells. In various embodiments, the intestinal submucosa tissue can be seeded with endothelial cells and one or more of these additional cell types (i.e., the intestinal submucosa tissue can be seeded with endothelial cells and one, two, three, etc. of these additional cell types).

DETAILED DESCRIPTION OF THE INVENTION

Figure 1:
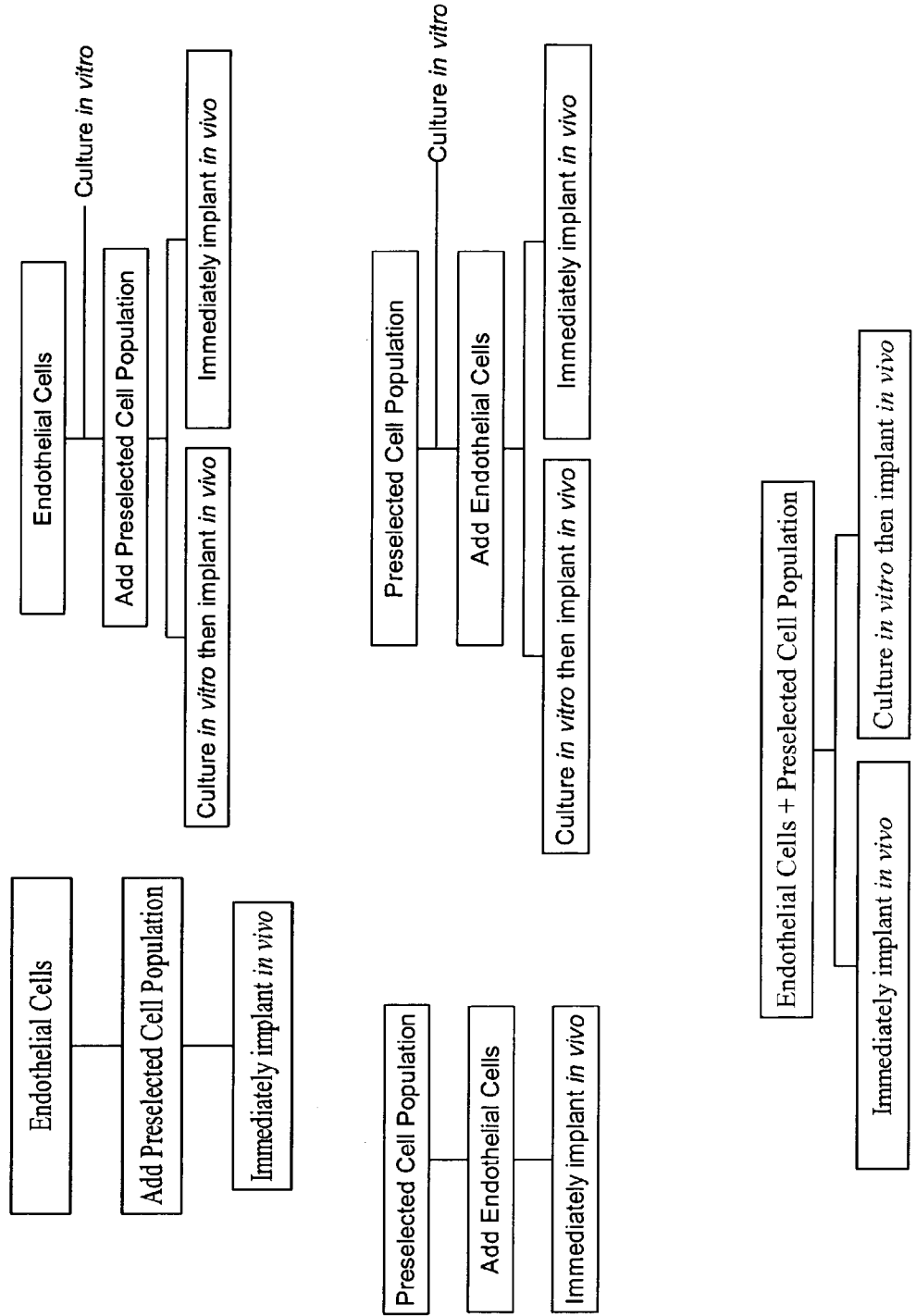
FIG. 1 provides flow charts depicting alternative preparations of the present graft construct.

The present invention is directed to a submucosa tissue graft construct comprising vertebrate intestinal submucosa tissue or other submucosa tissue, added endothelial cells and at least one additional preselected, exogenous population of cells. The acellular intestinal submucosa tissue is seeded with the endothelial cells and the preselected, exogenous population(s) of cells, and is used to repair diseased or damaged tissues. In accordance with the invention "damaged tissues" means tissues which are injured, lacerated, severed, or that have been surgically removed or are otherwise missing from the site in need of repair (e.g., congenital absence or deformity).

The endothelial cells for use in accordance with the invention can be derived from any type of endothelial cell population including macrovascular, microvascular, arterial, and venous endothelial cells. Either mature endothelial cells (e.g., harvested from an organ or a blood vessel) or endothelial cell precursors (e.g., progenitor cells or stem cells) can be used in accordance with the invention. Additionally, the endothelial cells can be harvested from a young or an old animal, but endothelial cells harvested from a young animal are preferred.

In one embodiment the additional preselected, exogenous population(s) of cells can comprise a population of non-keratinized or keratinized epithelial cells or a population of mesodermally derived cells selected from the group consisting of fibroblasts, smooth muscle cells, skeletal muscle cells, cardiac muscle cells, multi-potential progenitor cells, pericytes, osteogenic cells, or any other suitable cell type.

The additional preselected, exogenous population of cells, which is combined with the intestinal submucosa tissue and the endothelial cells, can be selected based on the cell type of the intended tissue to be repaired. For example, if skin is to be repaired, the preselected, exogenous population of cells can be non-keratinized epithelial cells or if cardiac tissue is to be repaired, the preselected, exogenous population of cells can be cardiac muscle cells. In another embodiment the intestinal submucosa tissue is seeded with autogenous cells isolated from the patient to be treated.

In one embodiment, the at least one additional preselected population of cells to be combined with the intestinal submucosa tissue and the endothelial cells includes smooth muscle cells and/or progenitor cells capable of differentiating into smooth muscle cells. Advantageously, the smooth muscle cells and/or smooth muscle progenitor cells can promote, along with the endothelial cells, the formation of vessels or vessel-like structures in the graft construct. In another embodiment, additional cell types can be added along with endothelial cells, smooth muscle cells, and/or smooth muscle cell progenitor cells.

In still another embodiment the at least one additional preselected, exogenous population of cells comprises a population of multi-potential progenitor cells. Intestinal submucosa tissue can induce the differentiation of these multi-potential progenitor cells into cells that assist in the repair of damaged tissues. Advantageously, intestinal submucosa seeded with a population of endothelial cells and a population of multi-potential progenitor cells can be implanted into a variety of different in vivo locations and the progenitor cells will differentiate into the appropriate cell type for the specific environment. For example, implantation of a composition comprising endothelial cells and multi-potential progenitor cells at the site of a tendon or a ligament will result in the graft construct remodeling into a tendon or a ligament.

The combination of intestinal submucosa tissue, endothelial cells, and an additional preselected, exogenous population of cells provides a tissue graft construct that shows surprisingly enhanced vascularization in vitro and/or in vivo leading to improved wound healing capabilities and better restoration of tissue function compared to the use of either intestinal submucosa tissue alone or intestinal submucosa tissue in combination with cell types other than endothelial cells as therapeutic agents.

In various embodiments, the intestinal submucosa tissue can be seeded with the additional preselected population of cells after the intestinal submucosa tissue is seeded with the endothelial cells, the intestinal submucosa tissue can be seeded with the additional preselected population of cells before the intestinal submucosa tissue is seeded with the endothelial cells, or the intestinal submucosa tissue can be seeded with the endothelial cells and the additional preselected population of cells simultaneously or nearly simultaneously (see FIG. 1 for various exemplary embodiments).

In one such embodiment, the intestinal submucosa tissue can be seeded with endothelial cells and the endothelial cells can be cultured on the intestinal submucosa tissue prior to the implantation of the construct into the affected region for a time sufficient to induce the formation of vessels or vessel-like structures. The intestinal submucosa tissue can be seeded with the at least one additional preselected, exogenous population of cells after the intestinal submucosa tissue is seeded with the endothelial cells and at any time up to just prior to implantation of the graft construct in vivo. Accordingly, depending on the time allowed for culturing the preselected population of cells on the intestinal submucosa tissue prior to implantation of the graft construct, the additional preselected population of cells may or may not be expanded (i.e., allowed to progress through at least one cell division cycle) prior to implantation of the graft construct into the affected region.

Alternatively, the intestinal submucosa tissue can be seeded with the at least one additional preselected, exogenous population of cells after the intestinal submucosa tissue is seeded with the endothelial cells, and the endothelial cells can be cultured on the intestinal submucosa tissue to expand the endothelial cells without inducing the formation of vessels or vessel-like structures or components prior to implantation of the graft. In this embodiment, depending on the time allowed for culturing the preselected population of cells on the intestinal submucosa tissue prior to implantation of the graft construct, the additional preselected population of cells may or may not be expanded prior to implantation of the graft construct into the affected region.

In another embodiment, the intestinal submucosa tissue can be seeded with the at least one additional preselected, exogenous population of cells after the intestinal submucosa tissue is seeded with the endothelial cells and the graft can be implanted soon thereafter without expansion of either the endothelial cells or the additional preselected, exogenous population of cells.

In an alternate embodiment, the intestinal submucosa tissue can be seeded with the additional preselected, exogenous population of cells and the preselected population of cells can be cultured on the intestinal submucosa tissue to expand (i.e., allow the cells to divide at least one time) the preselected cell population prior to implantation of the graft construct. In this embodiment, the intestinal submucosa tissue can be seeded with the endothelial cells after the intestinal submucosa tissue is seeded with the preselected population of cells and at any time up to just prior to implantation of the graft in vivo. Accordingly, depending on the time allowed for culturing the endothelial cells on the intestinal submucosa tissue prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the intestinal submucosa tissue can be seeded with the endothelial cells after the intestinal submucosa tissue is seeded with the at least one additional preselected, exogenous population of cells and the graft can be implanted soon thereafter without expansion of either the endothelial cells or the additional preselected, exogenous population of cells.

In yet another embodiment, the intestinal submucosa tissue can be seeded simultaneously or nearly simultaneously with the endothelial cells and the additional preselected, exogenous population of cells. In this embodiment, the endothelial cells and the additional preselected, exogenous population of cells can be cultured on the intestinal submucosa tissue to expand the two cell populations or the graft can be implanted without expansion of the two cell populations. If the endothelial cells are expanded, the expansion of the endothelial cells may or may not include the formation of vessels or vessel-like structures.

Intestinal submucosa tissue advantageously provides a physiological environment that supports the proliferation and differentiation of cells cultured in vitro on the intestinal submucosa tissue. Thus, cells can be seeded onto intestinal submucosa tissue and can be cultured using standard cell culture techniques, as described below, known to those of ordinary skill in the art, to produce tissue grafts for implantation into a host in need thereof.

The ability of intestinal submucosa tissue to provide a substrate that supports the growth of such cells provides the opportunity to expand the population of endothelial cells and/or the additional preselected, exogenous population of cells prior to implantation into a host. If endothelial cells are expanded, such expansion can result in the formation of vessels or vessel-like structures (i.e., potential vascularization of the graft construct in vitro) prior to implantation improving the wound healing capabilities of the graft upon implantation of the graft construct. The formation of vessels or vessel-like structures prior to implantation of the graft construct or, alternatively, the expansion of endothelial cells prior to implantation of the graft construct may improve the wound healing capabilities of the graft upon implantation such as by promoting differentiation and migration of cells growing on the abluminal side of the intestinal submucosa tissue sheet and by promoting proliferation of these cells within the intestinal submucosa tissue itself.

In embodiments where the added endothelial cells, and the additional preselected, exogenous population of cells are cultured on the intestinal submucosa tissue prior to implantation, the cells are cultured on the intestinal submucosa tissue under conditions conducive to cell growth. The cultured cells can be in either direct or indirect contact (e.g., fluid communication) with the intestinal submucosal tissue. Conditions conducive to cell growth are environmental conditions, such as sterile technique, temperature (e.g., about 37° C.) and nutrient supply, that are considered optimal for cell growth under currently accepted procedures for tissue and cell culture. Although optimum culture conditions depend on the particular cell type, cell growth conditions are generally well known in the art.

Intestinal submucosa tissue can be used in a variety of forms in accordance with this invention as a graft material and to culture endothelial cells and other cell types in vitro prior to implantation of the graft. These forms include a native sheet-like configuration, a gel form, a fluidized composition (e.g., by comminuting or digesting the tissue), and an extract for addition to art-recognized cell/tissue culture media. The intestinal submucosa tissue or component(s) thereof can provide a surface for cell adhesion and/or can induce cell differentiation and/or proliferation. The intestinal submucosa tissue is preferably sterilized prior to use in tissue/cell culture applications, however, nonsterile intestinal submucosa tissue can be used if antibiotics are included in the cell culture media.

In accordance with one embodiment of the present invention an intestinal submucosa tissue graft construct wherein the intestinal submucosa is delaminated from the tunica muscularis layer and at least the luminal portion of the tunica mucosa layer of the intestinal submucosa tissue is used as a graft material and to culture endothelial cells and other cell types in vitro prior to implantation of the graft construct. Intestinal submucosa tissue delaminated in this manner can be used in accordance with the invention in sheet form, in a gel form, as a fluidized composition such as a digest, or as an extract.

In one embodiment cells are seeded directly onto sheets of vertebrate intestinal submucosa tissue under conditions conducive to cell proliferation for culture of the cells prior to implantation of the graft construct. The porous nature of intestinal submucosa tissue allows diffusion of cell nutrients throughout the matrix. Thus, cells can be seeded onto and cultured on the luminal and/or the abluminal surface of the intestinal submucosa tissue sheet. The luminal surface is the intestinal submucosa tissue surface facing the lumen of the organ and is typically adjacent to an inner mucosa layer in vivo whereas the abluminal surface is the intestinal submucosa surface facing away from the lumen of the organ and is typically in contact with smooth muscle tissue in vivo.

Cells cultured on solid sheets of vertebrate intestinal submucosa tissue display a different growth pattern, and exhibit different interactions with the intestinal submucosa growth substrate, depending on which side of the intestinal submucosa sheet the cells are grown. Histological examination of endothelial cells cultured on intestinal submucosa tissue sheets in accordance with this invention reveals that the endothelial cells that are seeded onto the abluminal surface not only grow/proliferate along the surface of the intestinal submucosa tissue, but they also more readily migrate into and proliferate within the intestinal submucosa tissue itself. The luminal surface of the intestinal submucosa tissue comprises a more dense matrix than the abluminal side and, thus, cells are less likely to penetrate the luminal surface. Cells that are seeded onto the luminal surface of the intestinal submucosa tissue attach to the matrix but usually do not penetrate the surface of the matrix.

The endothelial cells and/or the additional preselected, exogenous population of cells seeded on intestinal submucosa tissue for culture prior to implantation of the graft construct can be grown in the presence of nutrients, including minerals, amino acids, sugars, peptides, proteins, or glycoproteins, such as laminin and fibronectin, and/or growth factors such as epidermal growth factor, vascular endothelial cell-derived growth factor, platelet-derived growth factor, platelet-derived growth factor-like molecules, transforming growth factor β, fibroblast growth factor, or another serum growth factor. In one embodiment fluidized or powder forms of intestinal submucosa tissue can be used to supplement standard cell culture media to enhance the capacity for sustaining and inducing the proliferation of the cells in vitro and to induce remodeling in vivo. The cells can be grown on the intestinal submucosa tissue in the presence of commercially available cell culture liquid media (either serum-containing or serum-free).

In one embodiment, the at least one additional preselected population of cells to be combined with the intestinal submucosa tissue and the endothelial cells can be smooth muscle cells and/or progenitor cells capable of differentiating into smooth muscle cells to promote, along with the endothelial cells, the formation of vessels or vessel-like structures in the graft construct. It is known that treatment of smooth muscle cells with a heparinase can induce a phenotypic change characteristic of proliferating cells. Accordingly, in embodiments where the intestinal submucosa tissue is seeded with endothelial cells and at least one preselected, exogenous population of cells including a smooth muscle cell population and/or a smooth muscle cell progenitor cell population a heparinase can be included in the cell culture medium. For example, 4 units/ml of a heparinase from *Flavobaterium heparinum* can be included in the culture medium for a short interval (e.g., 6 hours) or can be present continually in the culture medium.

It is also known that smooth muscle cells that are seeded on a substrate as a subconfluent monolayer of cells undergo a phenotypic change associated with the capacity to divide. The phenotypic change is inhibited if the smooth muscle cells are co-cultured with a confluent monolayer of endothelial cells. Accordingly, in embodiments where the intestinal submucosa tissue is seeded with endothelial cells and at least one preselected, exogenous population of cells including a smooth muscle cell population and/or a smooth muscle cell progenitor cell population the added endothelial cells can be seeded onto the intestinal submucosa tissue so that the cells attach to the intestinal submucosa tissue as a subconfluent monolayer of cells. In another embodiment the endothelial cells, smooth muscle cells, and/or smooth muscle progenitor cells can be seeded onto the intestinal submucosa tissue so that the cells attach to the intestinal submucosa tissue as subconfluent monolayers of cells.

It has been well documented that intestinal submucosa tissue is capable of inducing host tissue proliferation, remodeling and regeneration of appropriate tissue structures upon implantation in a number of microenvironments in vivo (e.g., tendon, ligament, bone, articular cartilage, artery, and vein). The use of such intestinal submucosa tissue in sheet form and fluidized forms for inducing the formation of endogenous tissues is described and claimed in U.S. Pat. Nos. 5,281,422 and 5,275,826, the disclosures of which are expressly incorporated by reference. Thus, the intestinal submucosa tissue grafts in accordance with the invention are implanted in vivo to induce remodeling of damaged tissues in need of repair.

In one embodiment, the claimed compositions comprising intestinal submucosal tissue, added endothelial cells, and an additional preselected, exogenous population of cells can be encapsulated in a biocompatible matrix for implantation into a host. The encapsulating matrix can be configured to allow the diffusion of nutrients to the encapsulated cells while allowing the products of the encapsulated cells to diffuse from the encapsulated cells to the host cells. Suitable biocompatible polymers for encapsulating living cells are known to those skilled in the art. For example a polylysine/alginate encapsulation process has been previously described by F. Lim and A. Sun (Science, Vol. 210, pp. 908-910). Indeed, vertebrate intestinal submucosa itself could be used advantageously to encapsulate the cells on an intestinal submucosa matrix in accordance with this invention for implantation as an artificial organ.

In one embodiment, a method is provided for enhancing the vascularization in vivo of an intestinal submucosa tissue graft construct. The method comprises the steps of seeding the intestinal submucosa tissue in vitro with a population of endothelial cells and at least one additional preselected, exogenous population of cells, and implanting the graft construct into a vertebrate at a site in need of repair. In one embodiment of this method, the intestinal submucosa tissue can be seeded with endothelial cells and the endothelial cells can be cultured on the intestinal submucosa tissue prior to the implantation of the construct into the affected region for a time sufficient to induce the formation of vessels or vessel-like structures. The intestinal submucosa tissue can be seeded with the at least one additional preselected, exogenous population of cells after the graft is seeded with the endothelial cells and at any time up to just prior to implantation of the graft in vivo. Accordingly, depending on the time allowed for culturing the preselected population of cells on the intestinal submucosa tissue prior to implantation of the graft construct, the additional preselected population of cells may or may not be expanded prior to implantation of the graft construct into the affected region.

Alternatively, the intestinal submucosa tissue can be seeded with the at least one additional preselected, exogenous population of cells after the intestinal submucosa tissue is seeded with the endothelial cells, and the endothelial cells can be cultured on the intestinal submucosa tissue to expand the endothelial cells without inducing the formation of vessels or vessel-like structures prior to implantation of the graft. In this embodiment, depending on the time allowed for culturing the endothelial cells on the intestinal submucosa tissue prior to implantation of the graft construct, the additional preselected population of cells may or may not be expanded prior to implantation of the graft construct into the affected region.

In another embodiment, the intestinal submucosa tissue can be seeded with the at least one additional preselected, exogenous population of cells after the intestinal submucosa tissue is seeded with the endothelial cells and the graft can be implanted soon thereafter without expansion of either the endothelial cells or the additional preselected, exogenous population of cells.

In an alternate embodiment of this method, the intestinal submucosa tissue can be seeded with the additional preselected, exogenous population of cells and the preselected population of cells can be cultured on the intestinal submucosa tissue to expand the preselected cell population prior to implantation of the graft construct. In this embodiment, the intestinal submucosa tissue can be seeded with the endothelial cells after the intestinal submucosa tissue is seeded with the preselected population of cells and at any time up to just prior to implantation of the graft in vivo. Accordingly, depending on the time allowed for expansion of the endothelial cells by culturing the cells on the intestinal submucosa tissue prior to implantation of the graft, the endothelial cells may or may not be expanded prior to implantation of the graft construct into the affected region. If the endothelial cells are expanded, the expansion of the endothelial cells may or may not include the formation of vessels or vessel-like structures.

In another embodiment, the intestinal submucosa tissue can be seeded with the endothelial cells after the intestinal submucosa tissue is seeded with the at least one additional preselected, exogenous population of cells and the graft can be implanted soon thereafter without expansion of either the endothelial cells or the additional preselected, exogenous population of cells.

In yet another embodiment, the intestinal submucosa tissue can be seeded simultaneously or nearly simultaneously with the endothelial cells and the additional preselected, exogenous population of cells. In this embodiment, the endothelial cells and the additional preselected, exogenous population of cells can be cultured on the intestinal submucosa tissue to expand the two cell populations or the graft can be implanted without expansion of the two cell populations. If the endothelial cells are expanded, the expansion of the endothelial cells may or may not include the formation of vessels or vessel-like structures.

A vascularized intestinal submucosa tissue graft construct for use in repairing diseased or damaged tissues is also provided in accordance with the invention. The vascularized graft construct comprises vertebrate intestinal submucosa tissue, added endothelial cells, and at least one additional preselected, exogenous population of cells wherein the endothelial cells have been cultured on the intestinal submucosa tissue for a time sufficient to form vessels or vessel-like structures in vitro.

In another embodiment, a method is provided for enhancing the vascularization in vivo of an intestinal submucosa tissue graft construct. The method comprises the steps of seeding the intestinal submucosa tissue in vitro with a population of endothelial cells and at least one additional preselected, exogenous population of cells, culturing in vitro the endothelial cells and the additional cell population on the intestinal submucosa tissue for a time sufficient to induce the formation of vessels or vessel-like structures, and implanting the graft construct into a vertebrate in a site in need of repair.

Intestinal submucosa tissue grafts can be seeded with initially small cell populations that can be expanded in vitro prior to implantation. Advantageously, seeding with endothelial cells can induce vascularization of the grafts in vitro upon culturing the endothelial cells in vitro on the intestinal submucosa tissue. The intestinal submucosa tissue can be further seeded with smooth muscle cells or smooth muscle cell progenitor cells or another cell type, such as fibroblasts, to promote vascularization.

In this embodiment, the intestinal submucosa tissue is seeded with endothelial cells and the endothelial cells are cultured on the intestinal submucosa tissue prior to the implantation of the construct into the affected region for a time sufficient to induce the formation of vessels or vessel-like structures. The intestinal submucosa tissue can be seeded with the at least one additional preselected, exogenous population of cells after the intestinal submucosa tissue is seeded with the endothelial cells and at any time up to just prior to implantation of the graft in vivo. Accordingly, depending on the time allowed for culturing the preselected population of cells on the intestinal submucosa tissue prior to implantation of the graft, the additional preselected population of cells may or may not be expanded prior to implantation of the graft construct into the affected region.

In an alternate embodiment, the intestinal submucosa tissue can be seeded with the additional preselected, exogenous population of cells and the preselected population of cells can be cultured on the intestinal submucosa tissue to expand the preselected cell population prior to implantation of the graft construct. In this embodiment, the intestinal submucosa tissue is seeded with endothelial cells after the intestinal submucosa tissue is seeded with the preselected population of cells. In this embodiment, the endothelial cells are cultured on the intestinal submucosa tissue for a time sufficient to allow for expansion of the endothelial cells to form vessel or vessel-like structures prior to implantation of the graft construct into the affected region.

In another embodiment, the intestinal submucosa tissue can be seeded with the endothelial cells and the additional preselected, exogenous population of cells simultaneously or nearly simultaneously. In this embodiment, the additional preselected, exogenous population of cells and the endothelial cells are cultured on the intestinal submucosa tissue to expand the two cell populations prior to implantation of the graft.

A method of preparing an intestinal submucosa tissue graft construct for use in repairing diseased or damaged tissues is also provided. The method comprises the step of seeding the intestinal submucosa tissue in vitro with a population of endothelial cells, and at least one additional preselected, exogenous population of cells to form the graft construct. The method can further comprise the step of culturing the endothelial cells on the intestinal submucosa tissue prior to the implantation of the graft construct into the affected region for a time sufficient to induce the formation of vessels or vessel-like structures.

The preparation of an intestinal submucosa useful in accordance with this invention is described in U.S. Pat. No. 4,902, 508. To summarize, the intestinal submucosa tissues are prepared from vertebrate intestine, preferably harvested from porcine, ovine or bovine species, but not excluding other species. In this regard, the intestinal submucosa tissues are typically xenogeneic (i.e., from a different species) but also can be allogeneic (i.e., from a nonidentical member the same species) or autogeneic (i.e., from the same animal or individual).

In one method to prepare the intestinal submucosa tissues for use in the invention, the tissues are subjected to abrasion using a longitudinal wiping motion to remove the outer layers, comprising smooth muscle tissues, and the innermost layer, i.e., at least the luminal portion of the tunica mucosa. Thus, the intestinal submucosa tissue is delaminated from the tunica muscularis and at least the luminal portion of the tunica mucosa. The intestinal submucosa is rinsed with saline and optionally sterilized; it can be stored in a hydrated or dehydrated state. Lyophilized or air dried intestinal submucosa can be rehydrated and used in accordance with this invention without loss of biological activity. Native intestinal submucosa as a starting material is a relatively acellular collagenous matrix and the preferred intestinal submucosa composition of the present invention is a collagenous matrix devoid of intact cells (i.e., the intestinal submucosa composition is acellular).

To form multilayer sheets of intestinal submucosa for use in the tissue grafts in accordance with the invention, multiple layers of intestinal submucosa can be overlapped with each other. The individual layers can be fixed to one another using standard techniques known to those skilled in the art, including the use of sutures and biocompatible adhesives such as collagen binder pastes. Alternatively, layers can be fused together by compressing the overlapped regions under dehydrating conditions, optionally with the addition of heat as described in U.S. Pat. No. 5,711,969, the disclosure of which is expressly incorporated herein.

The intestinal submucosa for use in the tissue graft can be sterilized using conventional sterilization techniques including glutaraldehyde tanning, formaldehyde tanning at acidic pH, ethylene oxide treatment, propylene oxide treatment, gas plasma sterilization, gamma radiation, electron beam and peracetic acid sterilization. Preferred sterilization techniques include exposing the intestinal submucosa tissue to peracetic acid, 1-4 Mrads gamma irradiation (more preferably 1-2.5 Mrads of gamma irradiation) or gas plasma sterilization; peracetic acid sterilization is the most preferred sterilization method. Typically, the intestinal submucosa is subjected to two or more sterilization processes. After the intestinal submucosa is sterilized, for example by chemical treatment, the tissue can be packaged and sterilized again using electron beam or gamma irradiation sterilization techniques. Typically, the cells are added to the graft tissue after sterilization of the graft. A sterilization technique such as that described in U.S. Pat. No. 6,206,931, incorporated herein by reference, may also be used.

It is also known that intestinal submucosa can be fluidized by comminuting and/or enzymatic digestion, without loss of its biological activity, for use in, for example, into the tissue grafts in accordance with the present invention. See U.S. Pat. No. 6,264,992 B1, the disclosure of which is expressly incorporated herein by reference. More particularly, the native or fluidized intestinal submucosa composition can be treated with an enzyme for a period of time sufficient to solubilize all or a major portion of the intestinal submucosa components. Preferably the intestinal submucosa is digested with an enzyme that hydrolyzes the structural components of the intestinal submucosa to produce a suspension or homogenous solution of intestinal submucosa components. The intestinal submucosa can be enzymatically treated with proteases (for example, a collagenase or trypsin or pepsin), glycosaminoglycanases or a combination of proteases and glycosaminoglycanases. Optionally, other appropriate enzymes can be used alone or in combination with proteases and glycosaminoglycanases. The tissue digest can be optionally filtered to provide a homogenous solution of partially solubilized intestinal submucosa.

The viscosity of fluidized intestinal submucosa for use in the tissue grafts in accordance with this invention can be manipulated by controlling the concentration of the intestinal submucosa component and the degree of hydration. The viscosity can be adjusted to a range of about 2 to about 300,000 cps at 25° C. Higher viscosity formulations, for example, gels, can be prepared from the intestinal submucosa digest solutions by dialyzing the digested material and then adjusting the pH of such solutions to about 5.0 to about 9.0.

The preparation of extracts of intestinal submucosa tissue is described in PCT Application No. PCT/US97/22721, published as WO 98/25964 on Jun. 18, 1998 incorporated herein by reference, and in Example 3. The fluidized and gel forms of the intestinal submucosa composition, and the extracts of intestinal submucosa may retain biologically active agents such as growth factors including transforming growth factor (TGF) β, TGF β-related proteins, and fibroblast growth factor.

The present invention also contemplates the use of powder forms of intestinal submucosa. In one embodiment a powder form of intestinal submucosa is prepared by pulverizing the intestinal submucosa under liquid nitrogen to produce particles ranging in size from 0.1 to 1 mm$^2$. The particulate composition is then lyophilized overnight and sterilized to form a solid substantially anhydrous particulate composite. Alternatively, a powder form of intestinal submucosa can be formed from fluidized intestinal submucosa by drying the suspensions or solutions of comminuted intestinal submucosa. A powder form of intestinal submucosa tissue could be combined, for example, with other components of the tissue graft such as cells and growth factors for use in accordance with this invention.

Example 1

Preparation of Fluidized Intestinal Submucosa

Small intestinal submucosa was harvested and prepared from freshly euthanized pigs (Delphi Indiana) as previously described in U.S. Pat. Nos. 4,902,508 and 4,956,178 and as described above. Intestinal submucosa was powderized under liquid nitrogen and stored at −80° C. prior to use. Partial digestion of the material was performed by adding 5 g powdered tissue to a 100 ml solution containing 0.1% pepsin in 0.5 M acetic acid and digesting for 72 hours at 4° C. Following partial digestion, the suspension was centrifuged at 12,000 rpm for 20 minutes at 4° C. and the insoluble pellet discarded. The supernatant was dialyzed against several changes of 0.01 M acetic acid at 4° C. (MWCO 3500). The solution was sterilized by adding chloroform (5 ml chloroform to 900 ml of 0.01 M acetic acid) to the intestinal submucosa tissue hydrolysate. Dialysis of the intestinal submucosa tissue was continued with two additional changes of sterile 0.01 M acetic acid to eliminate the chloroform. The contents of the dialysis bag were then transferred aseptically to a sterile container. The resultant fluidized composition was stored at 4° C. The fluidized intestinal submucosa composition is used in the graft constructs of this invention by combining the fluidized composition with other components such as cells and growth factors.

Example 2

Preparation of Intestinal Submucosal Gel Composition

To prepare the gel form of the intestinal submucosa, 8 mls of fluidized intestinal submucosa was mixed with 1.2 ml 10×PBS buffer (10× phosphate buffered saline containing 5 mg/L phenol red); 0.04 N HCl (approx 1.6 ml) was added to adjust the pH to between 6.6 and 7.4 and then 0.05 N NaOH (approx. 1.2 ml) was added to shift the pH to >8. The final volume was adjusted to 12 ml with water. The resultant mixture is combined with the other components of the graft construct such as cells and growth factors for implantation into a vertebrate host.

Example 3

Preparation of Intestinal Submucosal Extracts

Extraction buffers used for these studies included 4 M guanidine and 2M urea each prepared in 50 mM Tris-HCl, pH 7.4. The powder form of intestinal submucosa was suspended in the relevant extraction buffer (25% w/v) containing phenylmethyl sulphonyl fluoride, N-ethylmaleimide, and benzamidine (protease inhibitors) each at 1 mM and vigorously stirred for 24 hours at 4° C. The extraction mixture was then centrifuged at 12,000×g for 30 minutes at 4° C. and the supernatant collected. The insoluble material was washed briefly in the extraction buffer, centrifuged, and the wash combined with the original supernatant. The supernatant was dialyzed extensively in Spectrapor tubing (MWCO 3500, Spectrum Medical Industries, Los Angeles, Calif.) against 30 volumes of deionized water (9 changes over 72 hours). The dialysate was centrifuged at 12,000×g to remove any insoluble material and the supernatant was used immediately for combining with other components of the graft construct or lyophilized for storage.

Example 4

Sterilization of Intestinal Submucosal Tissue

Because cell culture techniques must be performed under strict aseptic conditions, if antibiotics are not included in the culture system, the intestinal submucosa tissue must be prepared in a sterile manner for use as a cell culture substrate before implantation of the graft construct. Numerous sterilization methods have been investigated to assess the effect of sterilization on the biotropic properties of intestinal submucosal tissue. Sterilization techniques which do not significantly weaken the mechanical strength and biotropic properties of the tissue are preferred. The following sterilization methods for intestinal submucosa have been evaluated: peracetic acid sterilization, 1.0 (or lower than 1.0) to 2.5 Mrad gamma-irradiation, 1.0 Mrad gamma-irradiation, Exspor (Alcide, Norfolk, Conn.) sterilization, e-beam, methylene oxide and various combinations of these sterilization methods. Gamma irradiation was performed on hydrated intestinal submucosal tissue using a $^{60}$Cobalt-gamma chamber. Exspor sterilization was performed according to manufacturer's specifications using a sterilant volume (ml) to intestinal submucosa (g) ratio of 10 to 1.

Various cell types (e.g., IMR-90, FR, HT-29, RPEC) were seeded upon the sterilized intestinal submucosa and their growth characteristics were analyzed at 1, 3, 7 and 14 days. Results obtained for all cell types showed that intestinal submucosal derived growth substrates sterilized by gamma irradiation or peracetic acid treatments supported some degree of adherence and growth of cells. However, cells seeded onto peracetic acid sterilized intestinal submucosal derived substrates showed increased adherence, increased survival, and enhanced rates of proliferation and differentiation. The preferred method for sterilization includes a peracetic acid treatment followed by terminal sterilization with gamma irradiation or e-beam.

Example 5

Sterilization of Intestinal Submucosal Tissue with Peracetic Acid

Intestinal submucosal tissue is soaked in a peracetic acid/ethanol solution for 2 hours at room temperature using a ratio of 10:1 (mls peracetic solution: grams intestinal submucosal tissue) or greater. The peracetic acid/ethanol solution comprises 4% ethanol, 0.1% (volume:volume) peracetic acid and the remainder water. The 0.1% peracetic acid component is a dilution of a 35% peracetic acid stock solution commercially available and defined as in Table 1. Preferably, the intestinal submucosal tissue is shaken on a rotator while soaking in the peracetic acid solution. After two hours, the peracetic acid solution is poured off and replaced with an equivalent amount of lactated Ringer's solution or phosphate buffered saline (PBS) and soaked (with shaking) for 15 minutes. The intestinal submucosal tissue is subjected to four more cycles of washing with lactated Ringer's or PBS and then rinsed with sterile water for an additional 15 minutes.

TABLE 1

Chemical Composition of the 35% Peracetic Acid Solution

| Composition, % by weight | |
|---|---|
| Peracetic acid | 35.5 |
| Hydrogen peroxide | 6.8 |
| Acetic acid | 39.3 |
| Sulfuric acid | 1.0 |
| Water | 17.4 |
| Acetyl peroxide | 0.0 |
| Stabilizer | 500 PPM |
| Typical active oxygen analysis, % by weight | |
| Active Oxygen as peracid | 7.47 |
| Active Oxygen as $H_2O_2$ | 2.40 |
| Total active oxygen | 10.67 |

Example 6

Growth of Endothelial Cells

Small intestinal submucosa is harvested and prepared from freshly euthanized pigs as described in U.S. Pat. No. 4,902,508. Following sterilization via various techniques (gamma irradiation, peracetic acid, etc.), the intestinal submucosa tissue is clamped within a polypropylene frame to create a flat surface area (50 mm$^2$) for cell growth. The frame is submerged in tissue culture medium to allow access of medium nutrients to both surfaces of the intestinal submucosa tissue. Endothelial cells are seeded (at 3×10$^4$ cells/intestinal submucosa tissue section) on the intestinal submucosa tissue and then placed in a 5% $CO_2$, 95% air incubator at 37° C. Following various periods of time, the seeded intestinal submucosa tissue is fixed in 10% neutral buffered formalin, embedded in paraffin, and sectioned (6 um). Various histological and immunohistochemical staining procedures are done to determine the endothelial cell growth characteristics. Vessels or vessel-like structures are observed using these procedures.

The invention claimed is:

1. A submucosa tissue graft construct, said tissue graft construct comprising vertebrate submucosa tissue, exogenously added endothelial cells, and at least one additional preselected, exogenous population of cells, wherein the tissue graft construct lacks vessels or vessel-like structures including the endothelial cells, and wherein the at least one additional preselected, exogenous population of cells is effective to enhance the initiation of formation of vessels or vessel-like structures including endothelial cells in said graft construct.

2. The graft construct of claim 1 wherein the submucosa tissue is delaminated from the tunica muscularis and at least the luminal portion of the tunica mucosa of said tissue.

3. The graft construct of claim 2 wherein the at least one additional cell population comprises a population of cells selected from the group consisting of keratinized epithelial cells, non-keratinized epithelial cells, and mesodermally derived cells.

4. The graft construct of claim 3 wherein the at least one additional preselected, exogenous population of cells is selected from keratinized and non-keratinized epithelial cells.

5. The graft construct of claim 2 wherein the at least one additional cell population comprises a population of smooth muscle cells.

6. The graft construct of claim 2 wherein the at least one additional cell population comprises a population of smooth muscle cell progenitor cells.

7. The graft construct of claim 2 wherein the submucosa tissue is seeded with the additional preselected population of cells after the submucosa tissue is seeded with the endothelial cells.

8. The graft construct of claim 1 further comprising a heparinase.

9. The graft construct of claim 1 further comprising a growth factor selected from the group consisting of vascular endothelial cell-derived growth factor, platelet-derived growth factor, a platelet-derived growth factor-like molecule, transforming growth factor β, and a serum growth factor.

10. The graft construct of claim 1 wherein the submucosa tissue is seeded with the endothelial cells after the submucosa tissue is seeded with the additional preselected population of cells.

11. The graft construct of claim 1 wherein the submucosa tissue is seeded with the endothelial cells and the additional preselected population of cells simultaneously or nearly simultaneously.

12. The graft construct of claim 1 wherein the submucosal tissue is in fluidized form.

13. The graft construct of claim 1 wherein the submucosal tissue is in powder form.

14. The graft construct of claim 1 wherein the submucosal tissue comprises multiple layers.

15. The graft construct of claim 1 wherein the construct is in the form of a sheet.

16. A vascularized submucosa tissue graft construct for use in repairing diseased or damaged tissues, said tissue graft construct comprising vertebrate submucosa tissue, exogenously added endothelial cells, and at least one additional preselected, exogenous population of cells wherein said endothelial cells have been cultured on said submucosa tissue for a time sufficient to form vessels or vessel-like structures in vitro wherein the at least one additional preselected, exogenous population of cells enhances the initiation of formation of vessels or vessel-like structures in said graft construct that lacks vessels or vessel-like structures.

17. The graft construct of claim 16 wherein the submucosa tissue is delaminated from the tunica muscularis and at least the luminal portion of the tunica mucosa of said tissue.

18. The graft construct of claim 16 wherein the submucosal tissue is in fluidized form.

19. The graft construct of claim 16 wherein the submucosal tissue is in powder form.

20. The graft construct of claim 16 wherein the submucosal tissue comprises multiple layers.

21. A submucosa tissue graft construct having vessel-like structures for use in repairing diseased or damaged tissues, said tissue graft construct comprising vertebrate submucosa tissue, exogenously added endothelial cells, and at least one additional preselected, exogenous population of cells, wherein said endothelial cells and said additional population of cells have been cultured together on the submucosa tissue from a time at which the graft construct lacked the vessel-like structures and wherein said additional population of cells has enhanced the initiation of formation of the vessel-like structures in said graft construct.

22. The graft construct of claim 21 wherein the at least one additional cell population comprises a population cells selected from the group consisting of keratinized epithelial cells, non-keratinized epithelial cells, and mesodermally derived cells.

23. The graft construct of claim 21 wherein the at least one additional cell population comprises a population of smooth muscle cells.

24. The graft construct of claim 21 wherein the at least one additional cell population comprises a population of smooth muscle cell progenitor cells.

25. The graft construct of claim 21 further comprising a heparinase.

26. The graft construct of claim 21 further comprising a growth factor selected from the group consisting of vascular endothelial cell-derived growth factor, platelet-derived growth factor, a platelet-derived growth factor-like molecule, transforming growth factor, and a serum growth factor.

27. The graft construct of claim 21 wherein the submucosa tissue is seeded with the additional preselected population of cells after the submucosa tissue is seeded with the endothelial cells.

28. The graft construct of claim 21 wherein the submucosa tissue is seeded with the endothelial cells after the submucosa tissue is seeded with the additional preselected population of cells.

29. The graft construct of claim 21 wherein the submucosa tissue is seeded with the endothelial cells and the additional preselected population of cells simultaneously or nearly simultaneously.

30. The graft construct of claim 21 wherein the submucosa tissue is delaminated from the tunica muscularis and at least the luminal portion of the tunica mucosa of said tissue.

31. The graft construct of claim 21 wherein the submucosal tissue is in fluidized form.

32. The graft construct of claim 21 wherein the submucosal tissue is in powder form.

33. The graft construct of claim 21 wherein the submucosal tissue comprises multiple layers.

* * * * *

UNITED STATES PATENT AND TRADEMARK OFFICE
CERTIFICATE OF CORRECTION

PATENT NO. : 7,815,686 B2 Page 1 of 1
APPLICATION NO. : 10/428350
DATED : October 19, 2010
INVENTOR(S) : Stephen F. Badylak It is certified that error appears in the above-identified patent and that said Letters Patent is hereby corrected as shown below:

Claim 26, Column 16, line 31 change "transforming growth factor" to "transforming growth factor β"

Signed and Sealed this
Fifteenth Day of March, 2011

David J. Kappos
*Director of the United States Patent and Trademark Office*